US009211165B2

(12) United States Patent
Jamison

(10) Patent No.: US 9,211,165 B2
(45) Date of Patent: Dec. 15, 2015

(54) POSITIONING AND INSTALLING SURGICAL DRILLING DEVICES AND RELATED DEVICES AND SYSTEMS

(71) Applicant: GRS Guide System, Inc., Beverly Hills, CA (US)

(72) Inventor: Mark Bennett Jamison, Los Angeles, CA (US)

(73) Assignee: GRS Guide System, Inc., Beverly Hills, CA (US)

( * ) Notice: Subject to any disclaimer, the term of this patent is extended or adjusted under 35 U.S.C. 154(b) by 0 days.

(21) Appl. No.: 14/679,285

(22) Filed: Apr. 6, 2015

(65) Prior Publication Data
US 2015/0265373 A1     Sep. 24, 2015

Related U.S. Application Data

(63) Continuation-in-part of application No. 14/255,654, filed on Apr. 17, 2014.

(60) Provisional application No. 61/955,447, filed on Mar. 19, 2014.

(51) Int. Cl.
A61C 3/00     (2006.01)
A61C 1/08     (2006.01)
A61C 3/02     (2006.01)

(52) U.S. Cl.
CPC .. *A61C 1/084* (2013.01); *A61C 3/02* (2013.01)

(58) Field of Classification Search
CPC ...... A61C 1/082; A61C 1/084; A61B 17/176; A61B 17/171; A61B 17/1725; A61B 17/1728; A61B 17/17
USPC ...................................... 433/172–176, 72–76
See application file for complete search history.

(56) References Cited

U.S. PATENT DOCUMENTS 2,317,648 A     4/1943   Siqveland
3,344,525 A     10/1967  Harris
(Continued)

FOREIGN PATENT DOCUMENTS

EP     1205159     5/2002
EP     1502556     2/2005
(Continued)

OTHER PUBLICATIONS

In2GuideTM Surgical Template Solution, http://www.kavo.com/Products/Dental-Imaging-Dental-X-ray/In2Guide%E2%84%A2.aspx, (Screenshot taken on Mar. 19, 2014).

*Primary Examiner* — Yogesh Patel
(74) *Attorney, Agent, or Firm* — Proskauer Rose LLP

(57) ABSTRACT

In some aspects, methods can include providing a top loading dental surgical guide including a dental drill guide positioning ring housed within the template material, the positioning ring including a body defining an inner surface and a retention element extending inwardly from the inner surface; coupling the surgical guide to the region to be drilled; temporarily engaging a drill guide within the positioning ring by axially coupling using the retention element, independently of a rotational motion of the drill guide relative to the positioning ring by engaging the retention element within a complementary recessed feature of the drill guide; performing a drilling procedure with a drill guided by the drill guide; and disengaging and removing the drill guide from the positioning ring.

19 Claims, 10 Drawing Sheets

(56) References Cited

U.S. PATENT DOCUMENTS

| | | | |
|---|---|---|---|
| 4,251,210 A | 2/1981 | Weissman | |
| 5,047,032 A | 9/1991 | Jellicoe | |
| 5,133,660 A | 7/1992 | Fenick | |
| 5,211,561 A | 5/1993 | Graub | |
| 5,320,529 A * | 6/1994 | Pompa | 433/76 |
| 5,800,168 A | 9/1998 | Cascione et al. | |
| 6,663,388 B1 | 12/2003 | Schär et al. | |
| 7,435,088 B2 * | 10/2008 | Brajnovic | 433/173 |
| 7,905,726 B2 | 3/2011 | Stumpel | |
| 7,942,668 B2 | 5/2011 | Brajnovic et al. | |
| 8,215,957 B2 | 7/2012 | Shelton | |
| 8,333,587 B2 | 12/2012 | Jamison | |
| 8,585,402 B2 | 11/2013 | Vogel et al. | |
| 2003/0149487 A1 | 8/2003 | Doubler et al. | |
| 2004/0219478 A1 | 11/2004 | Harter | |
| 2005/0170311 A1 | 8/2005 | Tardieu et al. | |
| 2008/0220390 A1 | 9/2008 | Klein | |
| 2009/0011382 A1 * | 1/2009 | Bavar | 433/76 |
| 2009/0286197 A1 | 11/2009 | Jamison | |
| 2010/0112520 A1 * | 5/2010 | Worthington | 433/169 |
| 2011/0159455 A1 | 6/2011 | Stumpel | |
| 2013/0302752 A1 | 11/2013 | Schneider | |

FOREIGN PATENT DOCUMENTS

| | | |
|---|---|---|
| EP | 1900338 | 1/2010 |
| WO | 2005055856 | 6/2005 |

* cited by examiner

POSITIONING AND INSTALLING SURGICAL DRILLING DEVICES AND RELATED DEVICES AND SYSTEMS

RELATED APPLICATIONS

This application is a continuation-in-part of U.S. patent application Ser. No. 14/255,654, filed Apr. 17, 2014, which claims the benefit of U.S. Provisional Patent Application No. 61/955,447, filed Mar. 19, 2014, entitled "Positioning and Installing Surgical Implants." The contents of the above applications are hereby incorporated herein by reference in their entirety.

TECHNICAL FIELD

This disclosure relates generally to surgical devices, and more specifically to positioning and installing surgical drilling devices and related devices and systems.

BACKGROUND

Implant dentistry typically involves restoring one or more teeth in a patient's mouth using artificial implants to support prosthetic crowns. The process for replacing a missing tooth typically involves placing an implant, adding a post (e.g., an abutment) to receive a crown, and adding a crown. A bone to be processed (e.g., the alveolar bone) can be first accessed through the patient's gum (gingival or attached) tissue. The specific site in the alveolar bone where the implant will be anchored can be prepared by drilling and/or reaming to accommodate the width of the dental implant to be inserted. The dental implant is then inserted into the hole, typically by screwing in a threaded connection, although other techniques can be used. A temporary healing cap is secured over the exposed proximal end in order to seal an internal bore of the implant. The patient's gums are usually then sutured over the implant to allow the implant site to heal and to allow desired osseointegration to occur, although other techniques can be used. Complete osseointegration typically takes anywhere from three to ten months. Alternatively, a temporary abutment and temporary cap can be placed immediately at the time of implant insertion. The restoration is completed by placing a post (abutment) to the implant and placing a cap over the post.

It is generally important that the implant be installed at a proper position and angle with respect to the particular structure of the alveolar bone. The implant should typically be installed within the alveolar bone for proper support and longevity of the implant. The implant should also be positioned optimally in order to place a functional and esthetic cap or prosthesis. Many techniques and devices have been developed and used for the correct placement of a dental implant. Many such techniques tend to depend on the skill and experience of the oral surgeon positioning and installing the implant.

SUMMARY

In some aspects, methods for forming an osteotomy site for a dental implant can include providing a top loading dental surgical guide comprising a template material that is configured to accommodate at least a portion of an edentulous alveolar ridge to support the orientation and guidance of surgical drills in a dental region to be drilled in a patient's mouth and a dental drill guide positioning ring housed within the template material, the dental drill guide positioning ring comprising: a substantially cylindrical body defining a longitudinal axis and an inner surface defining a central opening; and one or more flange retention elements extending inwardly from the inner surface of the cylindrical body; coupling the surgical guide along the portion of the edentulous alveolar ridge such that the dental drill guide positioning ring is oriented to guide one or more surgical drills to the dental region to be drilled; temporarily engaging a first drill guide within the dental drill guide positioning ring by axially coupling the first drill guide along its longitudinal axis with respect to the dental drill guide positioning ring, using the one or more protruding flange retention elements, independently of a rotational motion of the first drill guide relative to the dental drill guide positioning ring by engaging the one or more protruding flange retention elements within a complementary recessed feature of the first drill guide; performing a first drilling procedure with a first drill guided by the first drill guide; and disengaging and removing the first drill guide from the dental drill guide positioning ring.

Embodiments can include one or more of the following features.

The axially coupling of the first drill guide can include engaging the one or more flange retention elements within a recess of the first drill guide. The disengaging and removing the first drill guide can include gripping a handling tool retention feature of the first drill guide with a handling tool. The first drill guide can be removed from the dental drill guide positioning ring while the surgical guide remains coupled to the dental region. In some examples, each of the one or more flange retention elements can include an upper transition surface that tapers away from a top surface of the flange retention element; and a lower engagement surface that tapers away from a bottom surface of the flange retention element that is opposite the top surface and provides a predetermined resisting force to temporarily retain the guide within the dental drill guide positioning ring to limit axial separation of the drill guide from the dental drill guide positioning ring. In some embodiments, each of the one or more flange retention elements are positioned along a common plane substantially perpendicular to the longitudinal axis of the substantially cylindrical body.

In some examples, while temporarily engaged, the first drill guide can rotate within the drill guide positioning ring without disengaging. In some cases, the first drill guide can be free of handles to be held by a user during drilling. The first drilling procedure can be performed without a user handling the first drill guide once it is engaged within the dental drill guide positioning ring.

In some embodiments, the method also includes temporarily engaging a second drill guide within the dental drill guide positioning ring by axially coupling the second drill guide along its longitudinal axis with respect to the dental drill guide positioning ring, using the one or more protruding flange retention elements, independently of a rotational motion of the second drill guide relative to the dental drill guide positioning ring by engaging the one or more protruding flange retention elements within a recessed feature of the first drill guide; and performing a second drilling procedure with a second drill guided by the second drill guide.

In some embodiments, at least one of the first drilling procedure or second drilling procedure are performed without a user handling the first drill guide or second drill guide once engaged within the dental drill guide positioning ring. In some cases, all of the drilling procedures are performed without the user using any handled drill guides.

In some embodiments, the method also includes disengaging and removing the second drill guide from the dental drill guide positioning ring; and temporarily engaging a third drill guide within the dental drill guide positioning ring by axially coupling the third drill guide along its longitudinal axis with respect to the dental drill guide positioning ring, using the one or more protruding flange retention elements.

In some embodiments, the disengaging and removing the first drill guide from the dental drill guide positioning ring includes gripping a feature of the first drill guide with a handling tool and pulling the first drill guide from the dental drill guide positioning ring. The gripping the feature can include engaging resilient elements of the handling tool onto a lip feature of the first drill guide. The resilient elements of the handling tool can include finger-like elements and the lip feature of the first drill guide defines an annular recess in which the finger-like elements are disposed. In some embodiments, the temporarily engaging the first drill guide within the dental drill guide positioning ring includes gripping a feature of the first drill guide with a handling tool and inserting the first drill guide into the dental drill guide positioning ring. The gripping the feature can include engaging resilient elements of the handling tool onto a lip feature of the first drill guide. The resilient elements of the handling tool can include finger-like elements and the lip feature of the first drill guide defines an annular recess in which the finger-like elements are disposed.

In some aspects, methods for completing a drilling procedure to form an osteotomy site for a dental implant can include providing a top loading dental surgical guide comprising a template material that is configured to accommodate at least a portion of an edentulous alveolar ridge to support the orientation and guidance of surgical drills in a dental region to be drilled in a patient's mouth and a dental drill guide positioning ring housed within the template material, the dental drill guide positioning ring comprising: a substantially cylindrical body defining a longitudinal axis and an inner surface defining a central opening; and one or more flange retention elements extending inwardly from the inner surface of the cylindrical body formed along a common plane that is substantially perpendicular to the longitudinal axis; coupling the surgical guide along the portion of the edentulous alveolar ridge such that the dental drill guide positioning ring is oriented to guide one or more surgical drills to the dental region to be drilled; temporarily engaging a first drill guide within the dental drill guide positioning ring by axially coupling the first drill guide along its longitudinal axis with respect to the dental drill guide positioning ring, using the one or more protruding flange retention elements along the common plane, independently of a rotational motion of the first drill guide relative to the dental drill guide positioning ring by engaging the one or more protruding flange retention elements within a complementary recessed feature of the first drill guide, wherein the first drill guide is configured to freely rotate within the dental drill guide positioning ring; performing a first drilling procedure with a first drill guided by the first drill guide; and disengaging and removing the first drill guide from the dental drill guide positioning ring.

In some aspects, a dental surgical guide can include a template material configured to be coupled onto a portion of a patient's mouth; and a drill guide positioning ring attached to or integrally formed within the template material in a region to be drilled for installing a dental implant, the drill guide positioning ring comprising: one or more radial protrusion retention features to receive one or more dental drill guides, the retention features extending from an inner surface of the drill guide positioning ring and being configured to temporarily engage the drill guide, the temporary engagement axially coupling the drill guide along its longitudinal axis with respect to the drill guide positioning ring, the axial coupling being achieved independently from a rotational motion of the drill guide relative to the drill guide positioning ring.

Embodiments can include one or more of the following features. The one or more retention features can include one or more snap-fit features. The snap-fit features can include three partially circumferentially formed tabs extending inwardly from inner surface. The radial protrusion retention features can be configured to be received in a recess of the drill guide. The temporary engagement can permit the drill guide to freely rotate about its longitudinal axis within the drill guide positioning ring while engaged. The freely rotatability of the drill guide can limit a disengagement of the drill guide from the drill guide positioning ring based on contact between a dental drill and the drill guide. The dental surgical guide can be a top loading guide wherein the drill guides can be retained and released while the surgical guide remains coupled to the patient's mouth. The axial coupling of the drill guide can define a drilling distance from a top surface of the drill guide to a surface of the patient's mouth to be drilled. The template material can be fitted to and conform along an area of the patient's mouth adjacent to an area to be drilled. The drill guide can be limited from rotating within the drill guide positioning ring.

In some aspects, a drill guide positioning ring to be coupled to a template material of a surgical guide in a region to be drilled can include one or more retention protrusion features extending inwardly from an inner surface of the drill guide positioning ring to receive one or more drill guides, the retention features being configured to temporarily retain the drill guide within the drill guide positioning ring, wherein the temporary engagement axially couples the drill guide along its longitudinal axis with respect to the drill guide positioning ring, the axial coupling being achieved independently from a rotational motion of the drill guide relative to the drill guide positioning ring.

Embodiments can include one or more of the following features.

The surgical guide can be a dental surgical guide. The temporary engagement can permit the drill guide to rotate about its longitudinal axis without disengaging the drill guide from the drill guide positioning ring. The one or more retention features can include one or more snap-fit features disposed along an interior recess surface of the drill guide positioning ring. The snap-fit features can include at least one lip protrusion extending from the interior recess surface. The drill guide can include a detent along its outer surface and the drill guide positioning ring can include a surface configured to accommodate the detent during rotation of the drill guide. The free rotatability of the drill guide can limit a disengagement of the drill guide from the drill guide positioning ring based on contact between a dental drill and the drill guide. The drill guide positioning ring can be integrally formed within the template material. The surgical guide can be a top loading dental surgical guide wherein the drill guides can be retained and released while the surgical guide remains coupled to the patient's mouth. The axial coupling of the drill guide can define a drilling distance from a top surface of the drill guide to a surface of the patient's mouth to be drilled. The drill guide can be limited from rotating within the drill guide positioning ring.

In some aspects, a method for positioning surgical drill guides with respect to a surgical site to be drilled can include connecting a surgical ring to a template material that is configured to be fitted along a dental region to be drilled in a patient's mouth; and temporarily engaging a drill guide within the surgical ring using one or more radial protrusion retention features extending from an inner surface of the surgical ring, the temporary engaging including axially coupling the drill guide along its longitudinal axis with respect to the surgical ring, the axial coupling being achieved independently from a rotational motion of the drill guide relative to the drill guide positioning ring. In some embodiments, the connecting the surgical ring to the template material can include integrally forming the surgical ring within the template material.

In some aspects, a dental surgical guide can include a template material configured to be coupled onto a portion of a patient's mouth; and a drill guide positioning ring coupled to the template material in a region to be drilled for installing a dental implant, the drill guide positioning ring including an engagement portion comprising a region of radial interference between the drill guide positioning ring and an outer surface of one or more dental drill guides, the region of radial interference comprising one or more retention features extending from an inner surface of the drill guide positioning ring configured to engage a complementary undercut region defined along an outer surface of the drill guides, the region of radial interference being configured to temporarily engage the drill guides to axially couple the drill guide along its longitudinal axis with respect to the drill guide positioning ring, wherein the axial coupling is achieved independently from a rotational motion of the drill guide relative to the drill guide positioning ring. In some embodiments, the engagement portion configures the drill guide to at least partially rotate about its longitudinal axis within the drill guide positioning ring.

In some aspects, methods can include forming a physical model representative of a patient's mouth, the model defining a hole replicating a location for an implant (e.g., a dental implant) to be installed in the patient's mouth; disposing a locator device in the hole; and positioning, using the locator device, a drill guide positioning ring relative to portion of a surgical guide configured to be installed in the patient's mouth.

In some aspects, methods for forming a surgical guide (e.g., a dental implant surgical guide) can include forming a hole in a three dimensional physical model of a patient's surgical site (e.g., mouth), the hole replicating an intended implant hole location to be formed in the patient's surgical site (e.g., mouth); and using the hole to position a positioning ring within a surgical guide in order to accommodate one or more replaceable drill sleeves relative to a desired implant site in the patient's surgical site (e.g., mouth).

Embodiments can include one or more of the following features.

The hole in the model can be used to position the locator device in which to establish the precise orientation of the drill guide positioning ring for one or more replaceable drill sleeves temporarily retained within the surgical guide relative to a desired implant site in the patient's mouth. The method can also include forming the surgical guide over the drill guide positioning ring. Forming the surgical guide can include vacuum-forming a material layer over the model and drill guide positioning ring. The method can also include removing an excess portion of the surgical guide. The method can also include temporarily retaining one or more drill sleeves of a series of drill sleeves within the drill guide positioning ring. The series of drill sleeves typically comprise drill sleeves having increasing internal diameters to accommodate increasing diameter drills. The drill sleeves can be temporarily retained by one or more retention features along the drill guide positioning ring and/or the drill sleeves. The drill sleeves can be retained and removed from the drill guide positioning ring while the surgical guide is coupled to the patient's mouth. The model can be formed at least in part by taking a physical mold of the patient's mouth. The hole can be drilled in the model. The model can be formed at least in part by electronically scanning the patient's mouth. The electronically scanning can include taking a digital impression, x-ray, CT scan, or MRI. The hole can be electronically formed within the model using the software.

In some aspects, kits (e.g., assembly kits) for positioning a drill guide positioning ring for a surgical guide (e.g., a dental implant surgical guide) can include a locator device to be disposed in a locator hole defined within a physical model of a patient's surgical site (e.g., mouth), the hole replicating an intended implant hole location to be formed in the patient's surgical site (e.g., mouth); and a drill guide positioning ring to be coupled to a portion of the surgical guide, the drill guide positioning ring being configured to be releasably coupled to the locator device, the drill guide positing ring, the drill guide positioning ring defining an engagement region configured to temporarily retain one or more drill sleeve.

Embodiments can include one or more of the following features.

The kit can also include a cap that is configured to cover (e.g., temporarily cover) the engagement region of the drill guide positioning ring. The locator device can include a cylindrical (e.g., pin) region to be received within the locator hole. The drill guide positioning ring can be configured to be releasably coupled to the locator device by a press-fit joint in which the drill guide can snap into the surgical ring.

In some aspects, methods can include creating a model depicting at least a portion of a patient's surgical site (e.g., mouth); determining, using the model, an intended installed position of an implant (e.g., a dental implant) to be disposed within a bone region of the patient's surgical site (e.g., mouth); using the model, fabricating a surgical guide comprising a surgical ring to be positioned in relation to the intended position of the implant (e.g., a dental implant); coupling the surgical guide to the patient's mouth to position the surgical ring relative to the intended position of the implant (e.g., a dental implant); temporarily securing a first drill sleeve to the surgical ring and performing a first drilling operation; and with the surgical guide coupled to the patient's surgical site (e.g., mouth), removing the first drill sleeve from the surgical ring and temporarily securing a second drill sleeve to the surgical ring and performing a second drilling operation.

Embodiments can include one or more of the following features.

The creating a model depicting at least a portion of the patient's mouth can include electronically modeling the patient's mouth. The creating a model depicting at least a portion of the patient's mouth can include taking a physical mold of the patient's mouth. The creating a model can include forming dental model material or performing three-dimensional additive or subtractive manufacturing/modeling. The fabricating the surgical guide can include three-dimensionally additive or subtractive manufacturing/modeling (e.g., 3-D printing) a surgical guide. The fabricating the surgical guide can include creating a surgical guide using a physical model of the patient's mouth. The fabricating the surgical guide can include positioning the surgical ring relative to the physical model with a locator pin device. The fabricating the surgical guide can include vacuum-forming a sheet of material over the physical model and over the surgical ring positioned relative to the model. The securing the first or second drill sleeves in the surgical ring can include engaging a retention feature of the surgical ring. The engaging the retention feature of the surgical ring can include engaging a snap-fit connection between the surgical ring and the drill sleeve.

The surgical guide can be designed virtually through software to create a surgical guide consistent with a model depicting at least a portion of the patient's mouth. The fabricating of the surgical guide can include three-dimensionally additive or subtractive manufacturing/modeling. The fabricating of the surgical guide can include positioning the surgical ring relative to the intended implant location and orientation as designed virtually in the software. The fabrication of the surgical guide can provide a cylinder in which a surgical ring with internal retentive features can be inserted into the cylinder and secured to define the orientation and location of the virtual implant. The fabrication of the surgical guide can provide a surgical ring as an integrally formed feature of the surgical guide. The securing the first or second drill sleeves in the surgical ring can include engaging a retention feature of the surgical ring. The engaging the retention feature of the surgical ring can include engaging a snap-fit connection between the surgical ring and the drill sleeve.

Embodiments described herein can have one or more of the following advantages.

The systems and methods described herein for positioning surgical drill guides and surgical implants (e.g., dental implants) can help to provide a system for the creation of customizable surgical guides for many surgical (e.g., dental surgical) applications. The systems and methods described herein can typically be used with many conventional or currently available implant drills and stops from implant manufacturers or providers. In some cases, the systems and methods herein can provide a convenient, affordable, reusable, and accurate method for designing and fabricating surgical guides. Sequencing of multiple drill diameters can be achieved through the use of individual drill sleeves that fit into a single drill guide positioning devices (e.g., surgical rings) resulting in "hands-free" guidance for any or various sequences of drill diameters. The systems and methods described herein can help to provide a solution for surgical guide fabrication, with or without implant planning software, either in-office or through a dental laboratory.

In keeping with substantially universal applicability, the systems and methods described herein can help to provide comprehensive options for guiding drill sequences for any of various specific implant types and also for limitations presented by individual surgical procedures. Typically bound by specific anatomical features (e.g., tooth position, VDO, condylar rotation/translation, posterior/anterior intra-oral access, etc.), the systems and methods described herein allow for the individual drill sleeves to be positioned at any of various heights in order to achieve better surgical access. Unlike some conventional drill sleeves using handles or keys having varying platform heights that can be inconvenient or cumbersome and typically require a surgeon (or other trained individual) to physically hold the drill sleeve in position while drilling, the drill sleeves described herein can be individually inserted into and removed from a surgical guide for optimal surgical access and "hands-free" surgical guidance. Once a given surgical procedure has been completed, both the drill sleeves and drill stops discussed herein can be sterilized using various suitable methods and can be re-used in subsequent surgical procedures.

In some aspects, the surgical guides described herein position drill sleeves for better access and can generally be easily fabricated through 3-D modeling or simple vacuum forming techniques, so there is less of a significant need to maneuver around bulky, restrictive guide material. As a result of the universally designed surgical rings described herein, the guide systems described herein can provide a surgical platform from which guided surgery can now be used in a significantly greater variety of implant procedures, making safe surgical implant placement in a broad variety of scenarios possible for the surgeon/dentist and patient alike.

In some aspects, the surgical guides described herein can provide a system that is easier to use and to implement a drilling operation than by using some other conventional systems. For example, surgical guides described herein having a drill guide positioning surgical ring into which one or more of a series or drill sleeves can be temporarily secured (e.g., "snapped" into position) can allow a surgeon to place the series of drill sleeves into position for hands-free use. Also, in some embodiments, top-loading the drill sleeves into the surgical guide can allow for changing of drill sleeves (e.g., for increasing drill diameters) while the surgical guide remains connected to the patient's mouth.

Additionally, the surgical rings described herein can be configured to temporarily engage drill guides so that the drill guides are axially positioned (e.g., coupled to a surgical guide) but generally permitted to rotate (e.g., partially or freely rotated) within the surgical guide. In some embodiments, the temporary engagement between the drill guides and the surgical rings can be achieved using a snap-in type retention connection or by using a rotation-type device, such as a detent mechanism in one or more of the interfacing components. As discussed below, such free rotation of the drill guide without changing its longitudinal position can, in some cases, yield better performance of the surgical guide as a result of a reduced likelihood of inadvertently changing the drill guide position or ejecting the drill guide from the surgical guide during use. That is, as opposed to certain other types of surgical guides (e.g., that position a drill sleeve with a threaded or lure-type connection), a drill bit within a freely rotating drill guide is able to cause rotation of the drill guide (e.g., by contact or fluid contact) without inadvertently removing or impacting the desired positioning of the drill guide with respect to the implant site to be drilled.

In some embodiments, the term "freely rotate" can describe a configuration in which the drill guide is secured within a surgical ring and can rotate when turned by hand by a user. In some embodiments, the term "freely rotate" can describe a configuration in which the drill guide is generally secured within the surgical but can rotate when contacted (e.g., directly contacted) by a spinning drill guide. For example, the ability to rotate can serve a fail-safe (e.g., a mechanical fuse) to limit damage to the surgical guide or to the patient. In some embodiments, the term freely rotating describes a configuration in which drill guides can be engaged (installed) in the surgical ring and can be rotated within the surgical ring independently of such engagement. That is, rotational force exerted upon the drill guide (e.g., by hand or by a dental drill) typically does not affect in the installation of the drill guide and does not cause the drill guide to disengage from the surgical ring.

DETAILED DESCRIPTION

In some aspects, surgical guides, such as dental surgical guides to be coupled to a patient's mouth, can include drill guide positioning rings (e.g., surgical rings) that are configured to temporarily engage and axially couple drill positioning device (e.g., drill sleeves or drill guides) while permitting them to at least partially rotate (e.g., freely rotate (e.g., over 360 degrees)) within the surgical rings. In some embodiments, the term freely rotating describes a configuration in which drill guides can be engaged (installed) in the surgical ring and can be rotated within the surgical ring independently of such engagement. Such axial coupling and free rotation can help to create a surgical guide that is more reliable and easier to use by providing repeatability for positioning a series of drill guides. In some embodiments, the temporary engagement or retention of the drill sleeves within the surgical refers to attaching the drill sleeves without the use of additionally fasteners or components needed to couple the drill sleeve to the surgical ring.

Figure 1:
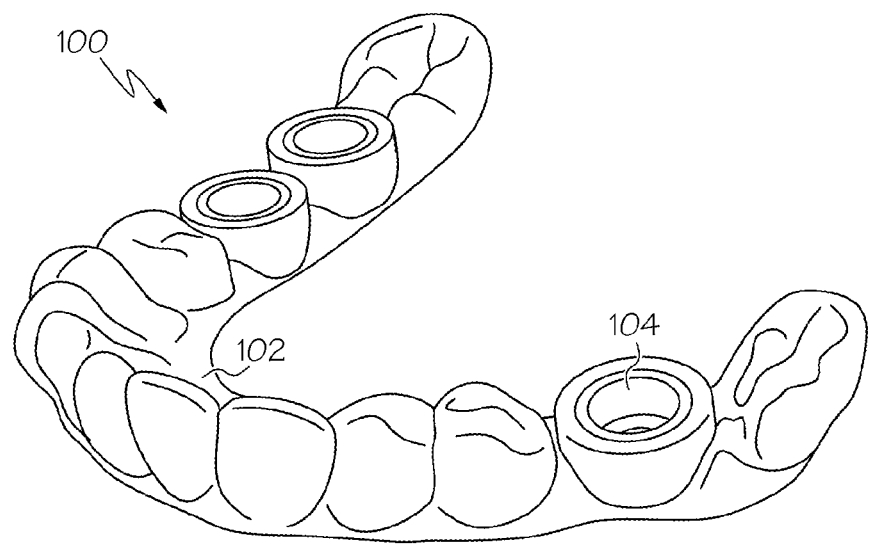
FIG. 1 is a perspective view of an example surgical guide having a surgical ring configured to retain and axially couple a drill guide.

Referring to FIG. 1, in some embodiments, a surgical guide (e.g., dental surgical guide) 100 can include a template material 102 and one or more surgical drill guide positioning devices (e.g., surgical rings) 104 disposed within the template material 102. The surgical guide 100 can be used to position drill guiding devices (e.g., drill guides or drill sleeves) relative to an intended surgical site to be drilled. While the surgical ring 104 is illustrated as being disposed substantially fully within the template material 102, other configurations are possible. For example, in some embodiments, the surgical ring (or substantially only the components of the surgical that interface with a drill guide) are connected to one or more template material sections that are configured to couple to a portion of the patient's mouth.

The template material 102 is formed and constructed to secure to a region of a patient's mouth, such as along one or more teeth, but can be fully edentulous. While the example illustrated is formed to secure to substantially an entire set of teeth (e.g., an entire bottom row), other configurations are possible. For example, the template material can be configured to connect to a smaller portion of the patient's mouth, such as one or two teeth, soft tissue only, bone only, or any combination thereof.

As discussed herein and detailed below, template materials can be formed by any of various suitable methods including additive manufacturing (3D printing), subtractive manufacturing (milling), vacuum-forming polymer sheets, or any of various other fabrication techniques.

Figure 2:
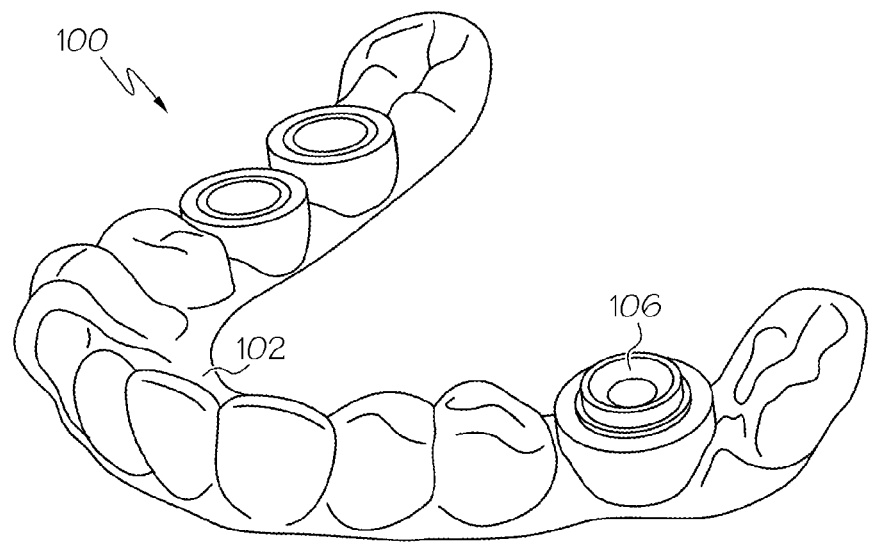
FIG. 2 is a perspective view of the surgical guide of FIG. 1 with a drill guide retained within the surgical ring.

The surgical ring 104 is configured to retain one or more drill guides, such as a series of drill guides that can be used to position a series of drills to be used in a surgical procedure. In some examples, the series of drills can be used to form a hole in a bone material to receive an implant device, such as a dental implant device. FIG. 2 illustrates a drill guide 106 installed in the surgical guide (e.g., within the surgical ring).

The surgical ring 104 is configured to connect (e.g., temporarily engage, retain, secure, or otherwise attach) the drill guide 106 axially to substantially couple the drill guide along its longitudinal axis with respect to the drill guide positioning ring. The connection of the drill guide 106 to the drill guide positioning ring can typically be achieved without the use of special tooling or fasteners, as well as independent of rotational motion of the drill guide relative to the drill guide positioning ring (e.g., as distinguished from using threaded or lure style (e.g., quarter turn) connection techniques. As discussed herein, longitudinal positioning of the drill guide with respect to the site to be drilled can help to drill to reliable and repeatable depths. Additionally, proper engagement of drill guides within the surgical guide can help limit drill guides from inadvertently being pulled by the drills (i.e., being lost in the mouth), thereby helping to make the surgical guides safer to use.

In addition to axial positioning, the surgical guide (e.g., the surgical ring) is also configured to allow rotation of the drill guide (e.g., free rotation (e.g., rotation beyond 180 degrees or beyond 360 degrees)) about its longitudinal axis. Free rotation of the drill guide can be useful as rotation of a drill can sometimes create rotational forces along a drill guide in which the drill is spinning. For example, in some cases, the drill can actually make contact with guide and the ability to freely rotate can help limit damage or friction that could otherwise occur. Additionally, in some cases, fluids (e.g., disinfectant, saliva, blood, or other fluids present in the mouth) in between the drill and the drill guide can move with the drill and impart a rotational force onto the drill guide. In addition to damage, in some cases, without such free rotation, rotational forces can cause drill guides, such as those that are connected by a threaded connection or merely placed into an opening, to disconnect from the from a surgical guide. Such disconnection could potentially cause damage to the equipment or harm to the patient.

Figure 3:
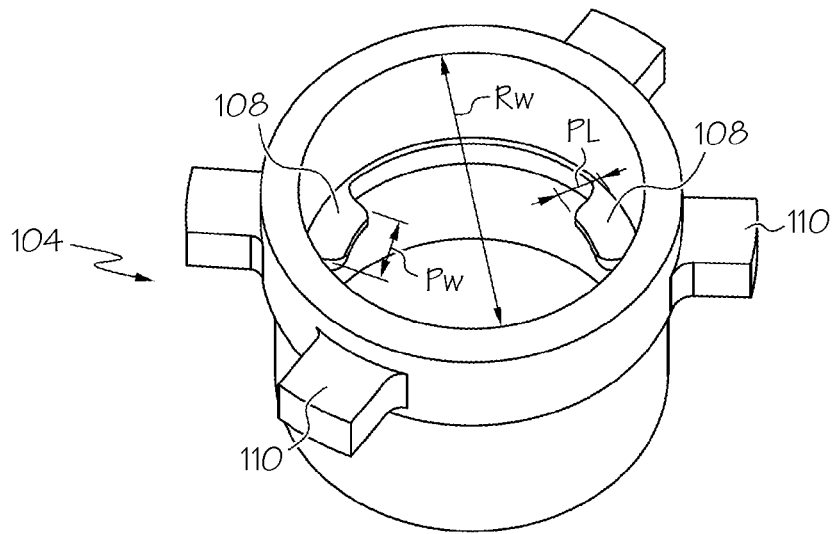
FIG. 3 is a perspective view of an example surgical ring having internal retention features configured to retain and axially couple a drill guide.

For the temporary engagement, the drill guide and/or the surgical ring can each or individually include retention features configured interface with the complementary components. The surgical ring can include one or more features along an engagement surfaces to engage the one or more surfaces of the drill guide to limit axial motion once the drill guide is installed in the surgical ring. For example, referring to FIG. 3, in some embodiments, the surgical ring 104 can include at least one retention element in the form of a protrusion (e.g., a lip, ridge, flange, or other type of feature) 108 configured to engage and retain a drill guide. In the example shown, the surgical ring 104 includes three protrusions 108 that extend inward radially into a central opening of the surgical ring. In some embodiments, the retention elements 108 can be arranged (e.g., disposed or formed) along a plane (e.g., a common plane) to engage and retain the drill guide. In an installed configuration, the retention elements along the common plane can be disposed in a recess of the drill guide. In some cases, the common plane can be substantially perpendicular to the surgical ring's longitudinal axis to be received within a complementary annular recess of the drill guide.

The protrusions 108 can be sized and constructed to apply a predetermined resisting force to an installed drill guide to limit the drill guide from moving axially within the surgical ring. The protrusions 108 can also be designed and constructed to resiliently deflect away from the longitudinal axis of the surgical ring to accommodate a tapered insertion end of the complementary drill guide and rebound to rest in an interfacing recess of the complementary drill guide to apply the resisting force. As illustrated, a protrusion 108 can have a radial protrusion length PL that it extends inwardly. In some examples in which the surgical ring inner width (e.g., diameter) Rw is about 5.3 millimeters (mm), the protrusion length PL can be about 0.65 mm to about 3.0 mm (e.g., about 1.27 mm). In some examples in which the surgical ring inner width (e.g., diameter) Rw is about 5.3 millimeters (mm), the protrusion length PL can be about 0.55 mm to about 0.7 mm (e.g., about 0.635 mm).

Additionally, the protrusions 108 can have a protrusion width Pw along which the protrusion can form an interface contact against an installed drill guide. In some examples in which the surgical ring inner width (e.g., diameter) Rw is about 5.3 mm, the protrusion width Pw can be about 1.0 mm to about 6.5 mm (e.g., about 2.8 mm). In some cases, the protrusions can be formed along various portions of the surgical ring inner surface. For example, the total protrusion width Pw (e.g., for an individual protrusion or as combined for all protrusions) can span along about 5% to about 100% (e.g., about 10% to about 50% (e.g., about 15% to about 30%) (e.g., about 25%)) of the circumference of the inner ring surface.

In some embodiments, the protrusions can span any of various angular lengths along the inner surface of the surgical ring. For example, a protrusion may extend about 30 degrees to about 90 degrees along the inner circumference of the surgical. In some examples, as illustrated, the surgical ring can include three protrusions that can each span about 30 degrees along the inner surface of the surgical ring.

While the protrusions 108 illustrated are generally equally spaced apart from one another, other embodiments are possible. For example, the surgical ring can include more or fewer protrusions, which can be spaced at various positions relative to one another or as a concentric ring. The surgical ring 104 can be formed of any of various types of structurally materials including various types of plastics or polymer materials. In some cases, the surgical ring 104 can be made of 3-D printable materials. The protrusions 108, for example, can be formed of flexible (e.g., flexibly resilient materials) materials, such as various plastics so that they can deflect when the drill guide is inserted.

The surgical ring can also have one or more installation features or surfaces. For example, the surgical ring 104 illustrated has multiple installation flanges 110 extending from its outer surface that can help secure the surgical ring to the template material during fabrication of the surgical guide. The surgical guide can have more or fewer installation features or can have an outer surface that is textured (e.g., knurled) to be secured to the template material. However, in some embodiments, the outer surface of the surgical can be smooth or otherwise lack such installation features or flanges.

Figure 4:
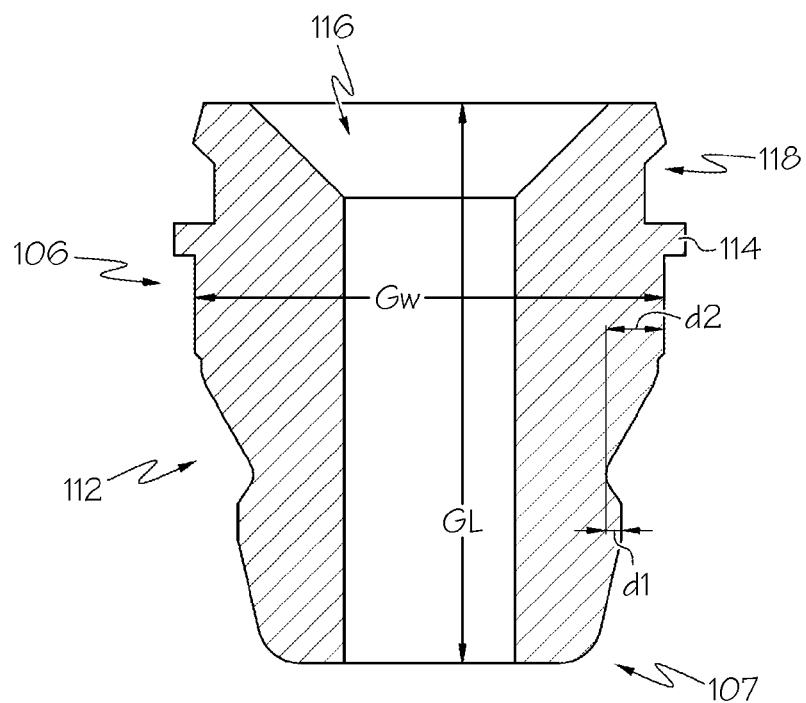
FIG. 4 is a side view of a drill guide illustrating example features to be retained within a surgical ring.

Drill guides can have one or more complementary features (e.g., a recess, an undercut region, an opening, or other type of complementary feature) to engage with the retention feature of the surgical ring (e.g., a protrusion of the surgical ring). Referring to FIG. 4, in some embodiments, the drill guide 106 defines a recess (e.g., a substantially circumferentially formed recess) 112. The recess 112 is sized and positioned to receive the retention elements (e.g., protrusions) 108 when the drill guide 106 is inserted into the surgical ring.

As illustrated, the drill guide 106 can include a substantially tapered insertion end 107 having an angled lead-in so that during insertion, the drill guide can gradually exert an outward radial force onto the surgical ring (e.g., onto the protrusions). In some examples, the insertion end 107 can include a taper lead in that is about 0 degrees to about 90 degrees (e.g., about 10 degrees to about 30 degrees (e.g., about 24 degrees)).

In some embodiments, the recess 112 can have any of various depths (e.g., radial widths) with respect to the other surfaces or features of the drill guide. For example, the recess can have a first depth (d1) from an outer surface of the tapered end 107. In some examples in which the drill guide length GL is about 7.2 mm and the drill guide width Gw is about 5.2 mm, the recess first depth d1 can be about 0.10 mm to about 1.5 mm (e.g., about 0.35 mm). In some examples in which the drill guide length GL is about 7.2 mm and the drill guide width Gw is about 5.2 mm, the recess first depth d1 can be about 0.10 mm to about 0.25 mm (e.g., about 0.175 mm).

Additionally, the recess 112 can have a second depth (d2) from the outer diameter of the drill guide. In some examples in which the drill guide length GL is about 7.2 mm and the drill guide width Gw is about 5.2 mm, the recess second depth d2 can be about 0.10 mm to about 2.0 mm (e.g., about 1.17 mm). In some examples in which the drill guide length GL is about 7.2 mm and the drill guide width Gw is about 5.2 mm, the recess second depth d2 can be about 0.40 mm to about 0.7 mm (e.g., about 0.585 mm).

While the recess 112 has been generally described and illustrated as being a continuously formed, circumferential recess, other configurations are possible. For example, the recess can be formed along only one or more portions of the drill guide. In some embodiments, the drill guide can include multiple recess segments to engage with the separated protrusions of the surgical ring. As a non-limiting example, the surgical ring can include three substantially equally spaced apart protrusions and the drill guide can include three or six equally spaced recess segments to engage and retain the protrusions. In some cases, one or more recess segments rather than a continuous circumferentially formed recess can help to limit a rotation of the drill guide relative to the surgical ring.

The drill guide 106 can be made of any of various types of structurally suitable materials. For example, the drill guide 106 can be made of durable materials such as metals (e.g., steels, stainless steels, aluminums, titanium, or other medically compatible metals). In some cases, the drill guide 106 can be made of durable metal materials that are configured to be sterilized (e.g., in an autoclave) so that they can be re-used in multiple procedures.

While certain dimensions have been provided as non-limiting examples, various components and features of the systems described herein can have other sizes. In some cases, the dimensions provided herein can establish a scale by which components or features can be sized relative to one another. That is, in some embodiments, components (e.g., the drill guides or the surgical rings) can be made smaller or larger and maintain a scaling of the component sizes as described herein. For example, a surgical ring can be made smaller or larger than the examples described above but can maintain a ratio of protrusion length or width to the surgical ring inner width as provided by the dimensional ranges listed above.

The drill guide can also include a seating feature (e.g., a flange) 114 that is configured to contact the surgical ring when the drill guide is installed to act as a stopping feature to limit insertion into the surgical ring. The seating flange 114 can also be used to set a distance (e.g., a predetermined distance) that the drill guide 106 is positioned from the drill site, such as a bone to be drilled, during use. To accommodate one or more drills, the drill guide defines a hole (e.g., a central hole) 116 through which a drill can pass during use.

As discussed below, the drill guide can also include one or more retention features that can be used to connect the drill guide to a handling tool. In the example illustrated, the handling tool retention feature can include a recess 118, which can be defined in part by a flange along an upper region of the drill guide.

Figure 5:
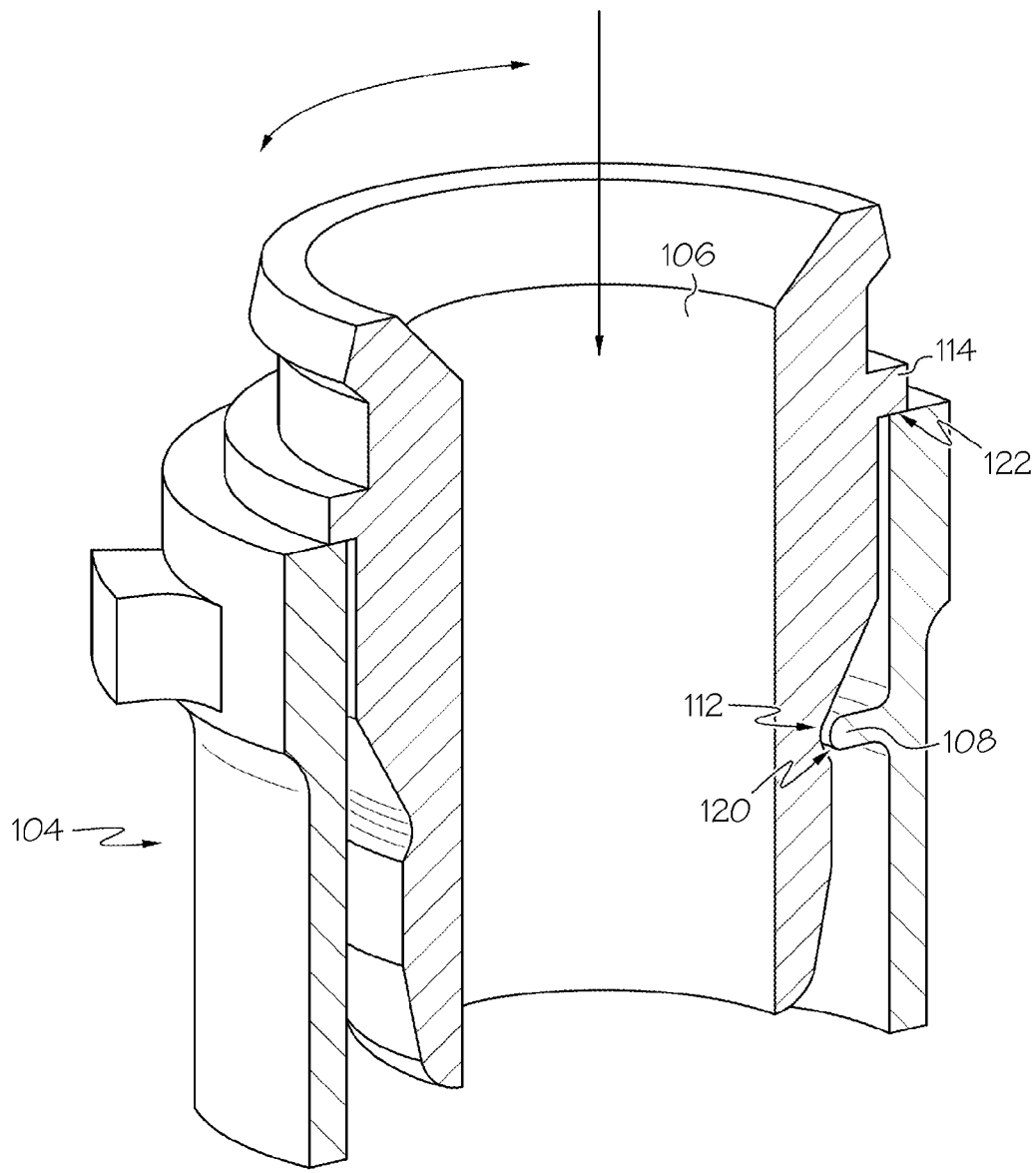
FIG. 5 is a cross-sectional view of a drill guide retained within a surgical ring, illustrating engagement features of the drill guide and the surgical ring that help to axially couple the drill guide within the surgical ring.

FIG. 5 illustrates an example engagement of a drill guide 106 within a surgical ring 104. As illustrated, once the drill guide 106 is inserted into the surgical ring 104, the protrusions 108 of the surgical ring can engage within the recess 112 of the drill guide. Once installed, the contact interface 120 between the protrusions and a surface of the recess helps to limit longitudinal motion of the drill guide relative to surgical ring. Additionally, in some embodiments, a contact interface 122 between the drill guide seating flange 114 and a seating surface of the surgical ring, alone or in combination with the contact interface 120, can help to limit longitudinal motion of the drill guide. However, the drill guide 106 is able to rotate about its longitudinal axis. As illustrated, in some embodiments, the protrusions 108 and the recess 112 can be separated radially by a slight spacing to help permit motion of the drill guide relative to the surgical guide. To help form proper fit between the drill guide and the surgical ring, the components can be designed to have a tight fit to help limit radial motion without being binding. For example, the drill guide width Gw typically has friction fit against the surgical ring width Rw. The friction fit can help to create a secure, stabilizing feature but can allow the drill guide to rotate. Additionally, protrusions can be designed to extend into the drill guide recess to also limit undesirable movement. For example, the recess second depth d2 can be about 0% to about 5% greater (e.g., 0% to about 3% (e.g., 0% to about 1%)) than the protrusion radial length PL.

For proper positioning of the drill guide after installation, the longitudinal spacing between the recess 112 and the flange 114 can be substantially the same as the longitudinal spacing between a top surface of the surgical ring and the protrusions 108.

While certain examples have been illustrated and described in which the surgical ring includes a protrusion and the drill guide includes a recess feature, other configurations are possible. For example, one or more protrusion features (e.g., any of those described herein) can be arranged on a drill guide and a complementary recess feature (e.g., any of those described) can be arranged on the surgical ring.

Additionally, while retention elements 108 have generally been described in the form of one or more protrusions, other configurations are possible. In some embodiments, one of the components (e.g., the drill guide or surgical ring) can include one or more rotational elements, such as bearing surfaces, detents (e.g., ball detents) or other suitable components, which can be configured to interface with a feature, such as a channel formed along the mating component. Detent type surfaces can be formed integrally within a component or can be attached (e.g., via a threaded or pressed connection). For example, the drill guide can include at least one ball detent extending from its outer surface and the surgical ring can include a recess (e.g., a channel) along its inner surface along which the ball can roll when installed.

While some drill guide and surgical ring examples have been described herein having certain retention/engagement features and techniques which, in some embodiments, can help the drill guide rotate (e.g., freely rotate) within the surgical guide, it is noted that such features can be implemented without requiring such free rotation. Specifically, in some embodiments, the drill guide and/or the surgical ring can include retention features but can also limit rotation of the drill guide to a certain angular rotation. For example, in some embodiments, a retention mechanism interface between a drill guide and a surgical ring can include one or more of the regions of radial interference as described herein (e.g., protrusions or detents that extend into a complementary recess) to axially position and couple the drill guide to the surgical ring but other features (e.g., of the drill guide or the surgical ring) can limit rotation of the drill guide. In some embodiments, the region of radial interference can include an undercut region, such as a recessed area in which a protrusion or detent can be disposed to retain the drill guide within the surgical ring.

Figure 6A:
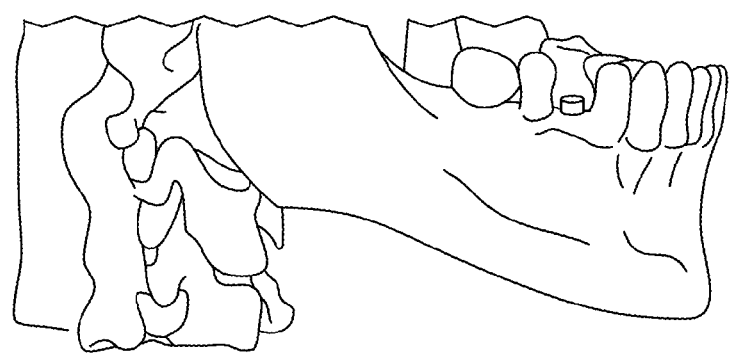
FIGS. 6A-6C illustrate an example method of manufacturing a surgical guide using dental implant planning software.

Surgical guides having the surgical rings described herein can be manufactured using any of various dental device fabrication methods or techniques. For example, referring to FIGS. 6A-6C, in some embodiments, dental implant planning software can be used to design a surgical guide with a properly positioned surgical ring. Specifically, as illustrated in FIG. 6A, dental implant planning software, such as coDiagnostix™ implant software, can be used to analyze a patient's condition to determine a desired position for a dental implant to be installed in the patient's mouth.

Figure 6B:
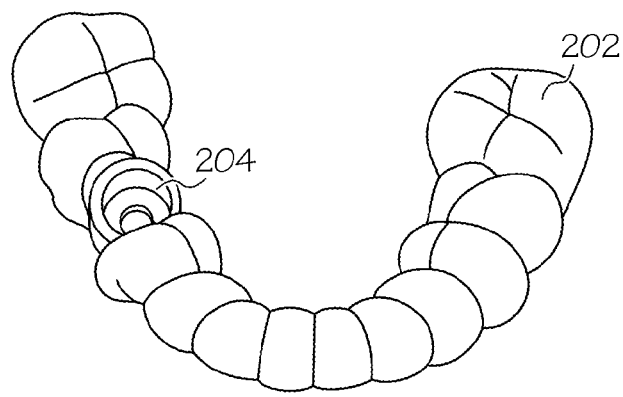

FIG. 6B illustrates an example surgical guide template material 202 designed using the implant planning software to specifically contour to the patients mouth (e.g., to the existing teeth). Using the implant planning software, the template material 202 can be designed to fit along the patient's specific oral anatomy (e.g., a configuration and layout or one or more bones, teeth, or soft tissue within the mouth). A recess (e.g., a hole) 204 can be designed within the template material to receive a surgical ring as described herein. However, in some embodiments, a surgical ring can be designed as an integral component of the template material (i.e., as opposed to a simple hole in which the surgical ring is installed). The recess 204 is typically positioned such that once the surgical ring is connected to the template material, drill guides installed within the surgical ring are disposed at a known (predetermined) distance from the intended implant site.

Figure 6C:
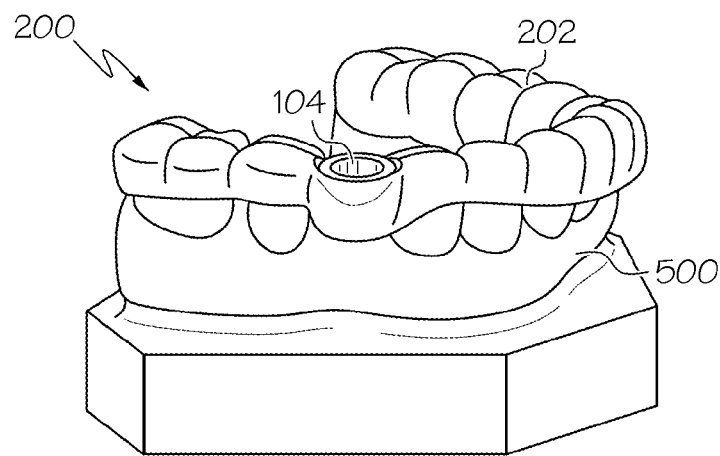

FIG. 6C illustrates a fabricated surgical guide 200 with the surgical ring 104 installed, where the surgical guide 200 is installed on a model 500 of a portion of a patient's mouth. The surgical guide template 202 can be formed of any of various structurally suitable materials and can be manufactured by any of various suitable techniques. For example, the surgical guide template 202 can be formed by additive manufacturing (3D printing), subtractive manufacturing (milling), or other suitable manufacturing methods. Once the template 202 is fabricated, the surgical ring 104 can be secured within the template 202. For example, the surgical ring 104 can be bonded (e.g., using light-cured bonding agents or other types of adhesives) or secured by a tight press-fit connection.

In addition to designing and manufacturing a surgical guide using software based positioning methods, physical models depicting the patient's mouth can be formed and used to manually fabricate a surgical guide conforming to the model. An example of such a fabrication method is illustrated in FIGS. 7A-7F. Specifically, referring to FIG. 7A, a model 500 of the patient's mouth can be made having a hole 502 in a location in which the desired implant is to be installed in the patient's mouth. As discussed herein and detailed below, the model can be designed and formed using various conventional dental implant planning software programs and manufacturing techniques or by various known dental molding and casting techniques.

Figure 7A:
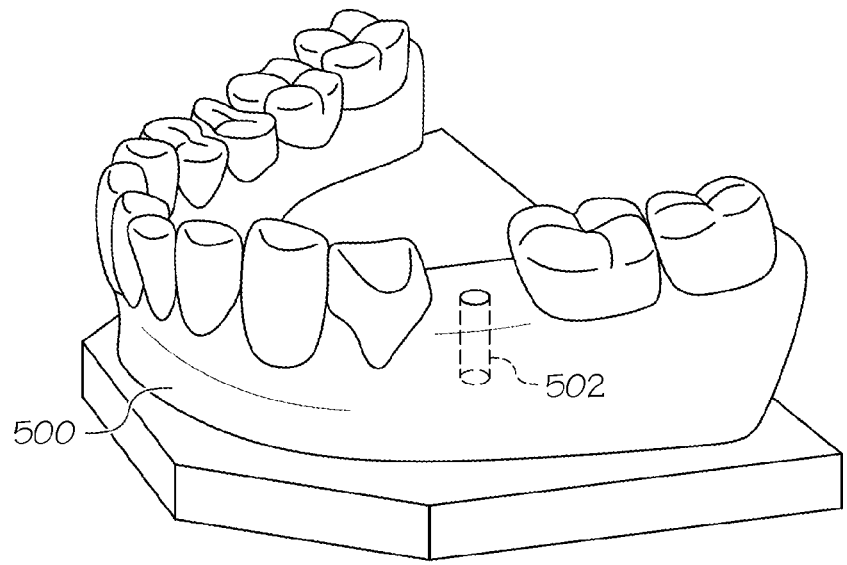
FIGS. 7A-7F illustrate another example method for manufacturing surgical guide in which a physical model is used to position a surgical ring for joining to a template material to be secured to a patient's mouth.
Figure 7B:
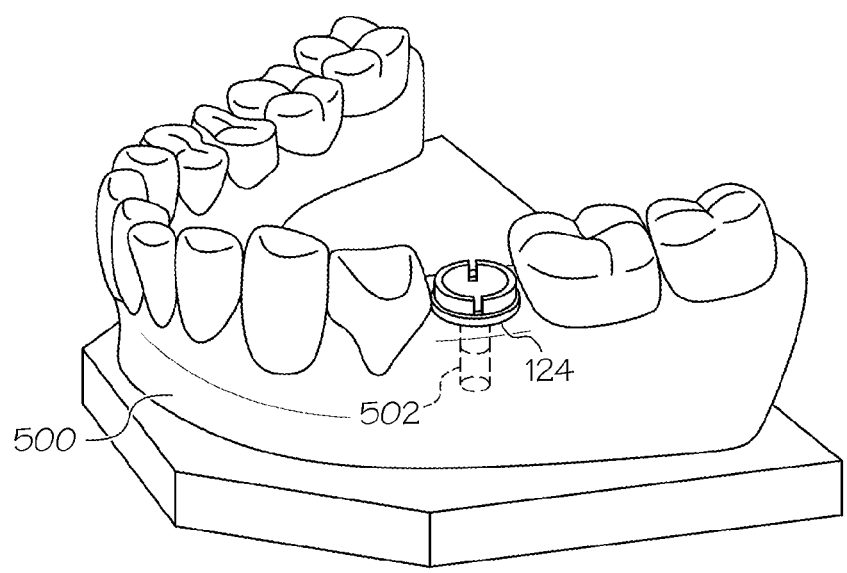

Referring to FIG. 7B, a surgical ring locator device (e.g., a locator pin) 124 can be disposed within the hole 502 of the model to serve as a datum structure for positioning components of the surgical guide. In some embodiments, particularly for models formed using implant software, the locator device can be manufactured as a post or pin extending from the physical model rather than a hole in which a pin is disposed.

Figure 7C:
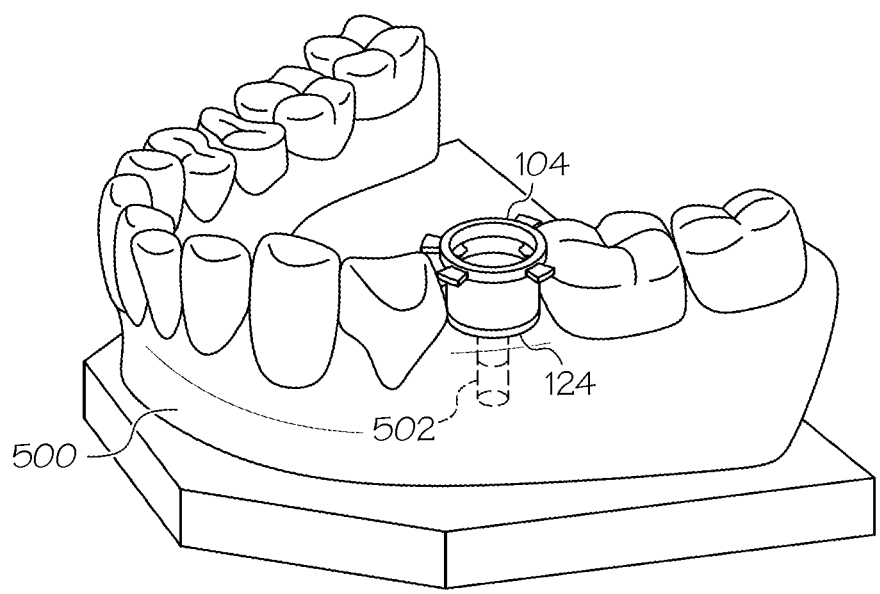
Figure 7D:
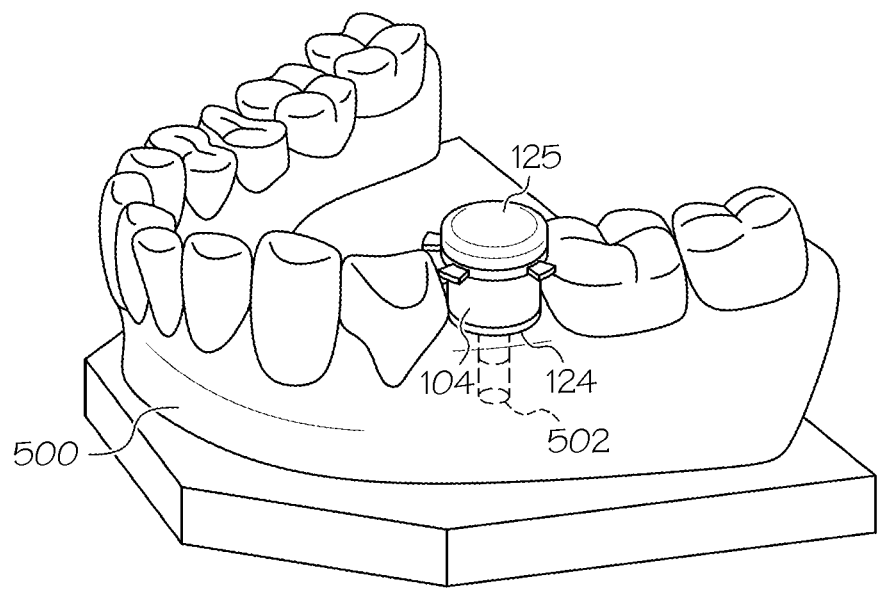

Referring to FIG. 7C, a surgical ring 104 can be placed on top of the locator pin 124. The locator pin 124 is typically configured to position the surgical ring 104 in a location relative to the model 500 that is representative of its desired final location in the surgical ring when the surgical guide is installed onto the user's teeth. Next, referring to FIG. 7D, a cap (e.g., a protective cap) 125 can be installed on top of the surgical ring 104. For example, the cap 125 can be used to cover and protect internal features and components of the surgical ring during subsequent fabrication processes.

Figure 7E:
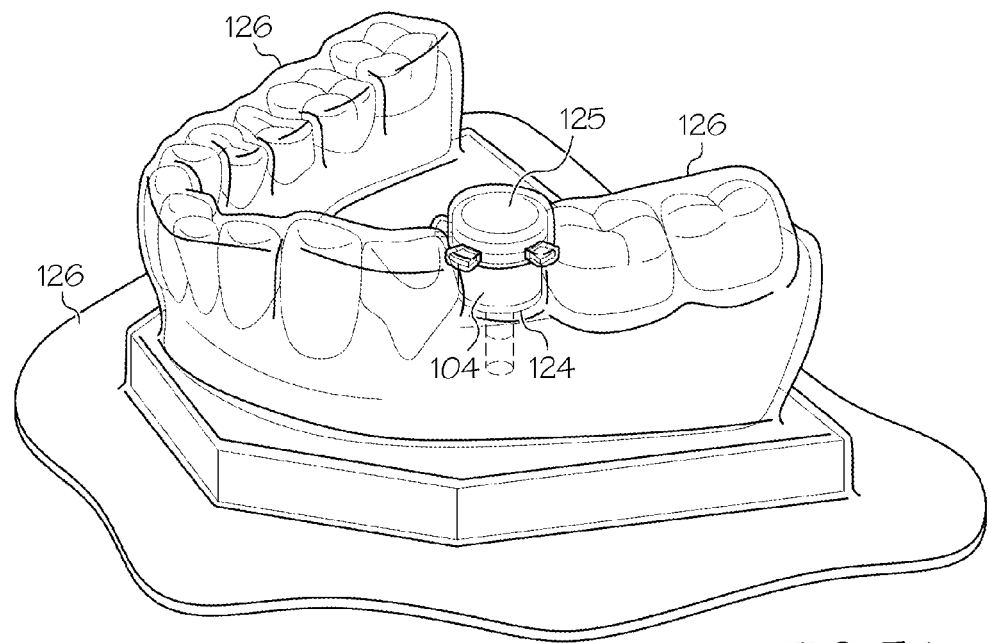

As illustrated in FIG. 7E, the physical model having the surgical ring 104 positioned relative to the desired implant site (e.g., using a locator pin 124 and a cap 125) can be formed in a template material conforming to the oral anatomy of the model. For example, a polymer sheet 126 can be vacuum-formed over the model and surgical ring to couple (e.g., bond or attach) the surgical ring to the formed polymer sheet. As illustrated, the vacuum-formed polymer sheet generally conforms to the various features of the model so that the resulting surgical guide fits onto the model and therefore also onto the patient's actual teeth.

Figure 7F:
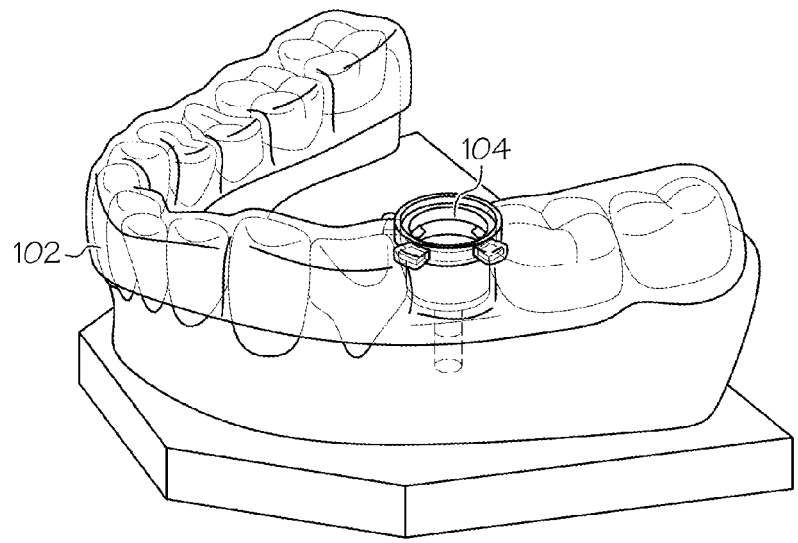

To form the surgical guide, as depicted in FIG. 7F, the vacuum-formed template material 102 can be trimmed from excess vacuumed-formed sheet around the periphery of the teeth. Additionally, the sheet can be trimmed from a top region of the surgical ring to expose its internal features for engaging the drill guide. Also, with the top surface exposed, the cap can be removed.

Figure 8A:
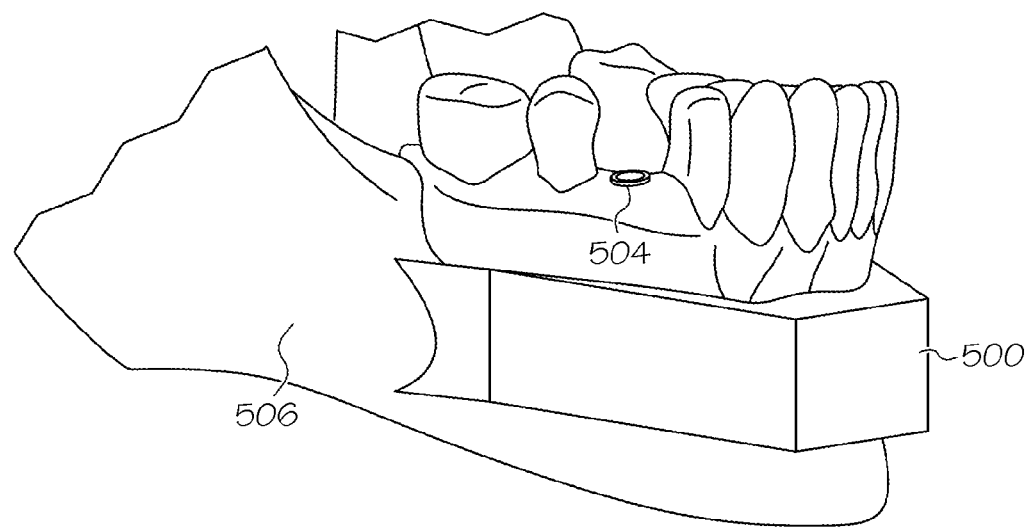
FIGS. 8A and 8B illustrate an example method for creating a three-dimensional model with an intended implant hole using dental implant planning software.
Figure 8B:
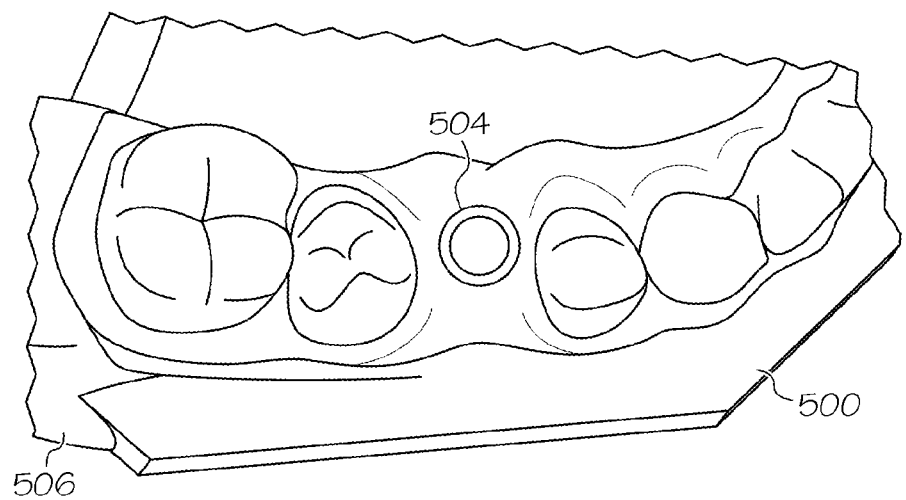

As discussed herein, the physical model 500 having a hole 502 formed to simulate the desired implant location can be formed by any of various methods including using dental implant software or conventional mold and casting techniques. For example, FIGS. 8A and 8B illustrate an example in which dental implant planning software is used to form a three dimensional model having a hole in a desired implant position. Specifically, the implant planning software can be used to assist in locating the desired implant 504 along the illustrated patient bone structure 506. Using the software, an electronic model 500 of the patient's oral anatomy can be created and overlaid with the bone structure (e.g., produced by three-dimensional X-rays) 506. Once the model 500 and the bones 506 align with one another, a desired implant hole can be created in the electronic model. Once the electronic model is created, a physical model can be fabricated by any of various manufacturing techniques such as additive manufacturing (3D printing) or subtractive manufacturing (machining (e.g., milling)). As mentioned above, rather than a hole to receive a locator pin, the software can be used to manufacture the locator pin or post onto the physical model itself.

Additionally or alternatively, a physical model having a hole can be formed by other techniques, such as taking a direct mold of the oral anatomy and creating a model of the oral anatomy (e.g., a dental impression). In some cases, the impression can be a stone or plaster impression. To position the hole, a surgeon can use any of various conventional techniques to estimate the desired implant position and can manually form (e.g., drill) the hole directly into the impression.

Figure 9:
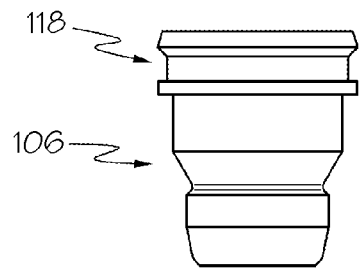
FIG. 9 is a side view of an example drill guide defining engagement features for retention within a surgical ring, as well as engagement features for retention within a drill guide handling tool.
Figure 10:
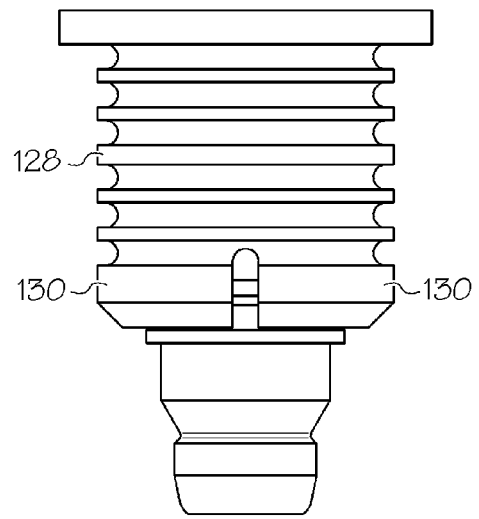
FIG. 10 is a side view of an example drill guide disposed within an example drill guide handling tool.
Figure 11:
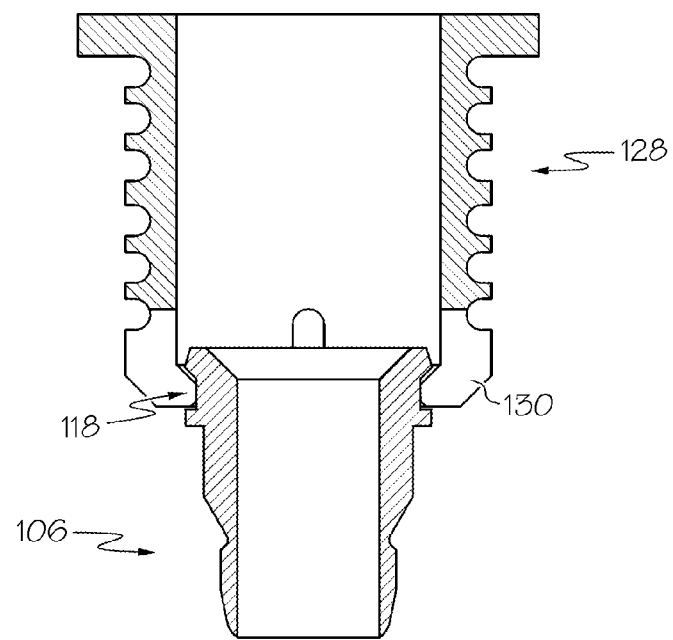
FIG. 11 is a cross-sectional view of a drill guide retained within a drill guide handling tool, illustrating engagement features of the drill guide and the handling tool.

Once a surgical guide is formed, drill guides can be retained within the guide's surgical ring to form a series of holes to install a dental implant. In some embodiments, the drill guides discussed herein can include one or more features to promote engagement with one or more handling tools, which can make it easier to handle and install the drill guides during use. Referring to FIG. 9, a drill guide 106 can include one or more retention features 118 arranged along its upper region that are configured to be gripped or retained by a handling tool 128. Referring to FIGS. 10 and 11, the retention feature can include recess (e.g., defined in part by a flange) 118 that can be gripped and engaged by protrusions (e.g., finger-like elements) 130 of a handling tool 128.

As illustrated, in some embodiments, an engagement end of a handling tool can include multiple finger-like elements 130 each separated by a spacing such that each of the finger-like elements can move semi-independently from one another. Such independent movement can help the handling tool attach and detach from drill guides. In some embodiments, the spacing separating the finger-like elements can be positioned at substantially equal distances from one another. In the example illustrated, the handling tool has four finger-like elements substantially equally spaced around the engagement end of the handling tool.

In some cases, the handling device can be configured to retain a drill guide for removal of the drill guide from a storage cassette, insert the drill guide into the surgical guide, and remove the handling device from the drill guide so that a hole can be drilled. Additionally, in some cases, the handling device (e.g., the same device used to install the drill guide or a different device) can be used to connect to an installed drill guide, remove the drill guide from the surgical guide, and remove the drill guide from the handling device. In some cases, a removal handling device can have a tighter engagement fit with the drill guide than that of an insertion handling tool.

Figure 12A:
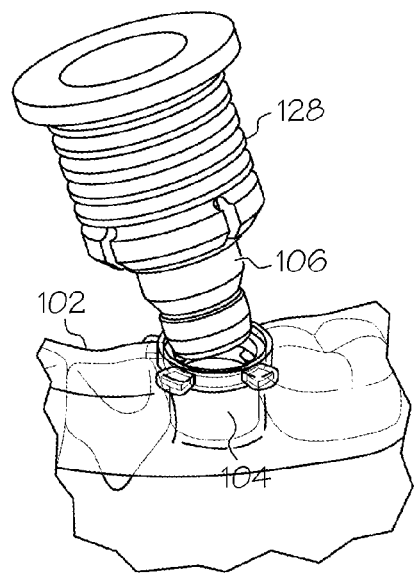
FIGS. 12A-12C illustrate an example method of installing a drill guide into a surgical guide using a drill guide insertion tool.
Figure 12B:
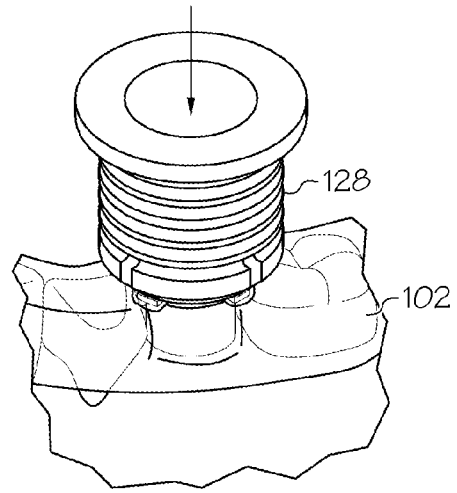
Figure 12C:
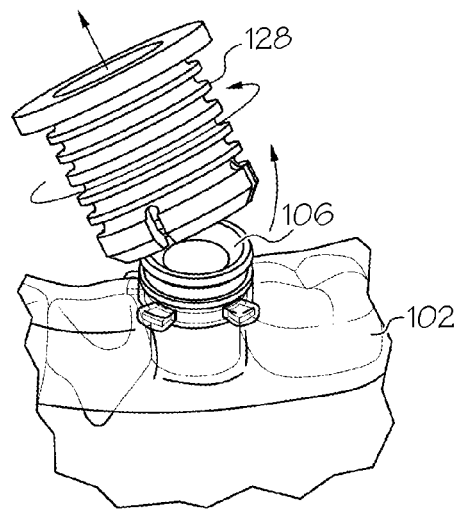

FIGS. 12A-12C illustrate an example insertion sequence in which the drill guide can be installed in a surgical ring. FIG. 12A illustrates a surgical guide installed onto a model of a patient's mouth. For installation, the drill guide 106 can be handled by the handling device 128 and inserted into the surgical ring 104. The drill guide can be generally inserted axially into the surgical ring and pushed inwardly until the retention features of the surgical ring and/or the drill guide engage and axially couple the drill guide within the surgical ring, as illustrated in FIG. 12B. For example, flange-type retention features along the inner surface of the surgical ring can snap into a recess along an outer surface of the drill guide. In some embodiments, an audible indication (e.g., a "click") may be emitted when the drill guide is engaged in the surgical ring.

Once the drill guide is engaged within the surgical guide, the handling tool can be removed. In some embodiments, referring to FIG. 12C, the handling device can be designed such that it can be rolled off of the drill guide so as to limit the drill guide from inadvertently being pulled out of the surgical ring when the handling device is pulled from the drill guide. In some embodiments, having multiple finger-like elements 130 (e.g., and the spacing therebetween) can contribute to the handling device's ability to be rolled and pulled off of the drill guide.

Removal of the drill guide can be performed in a similar manner to insertion. For example, a drill guide handling tool (e.g., the same tool used for insertion or a different tool which can be specific for removal) can be connected to a drill guide by being pressed onto an upper region of the drill guide. The drill guide can then be pulled from the surgical ring. In some cases, the handling tool can be gripped around its sides (e.g., on or near the retention elements) to limit the drill guide from being disconnected from the handling tool as the drill guide is pulled from surgical ring. Additionally, in some embodiments, a removal handling tool can be designed and configured to have a tighter fit with the drill guide to limit the drill guide from inadvertently disconnecting from the handling tool prior to removal.

While the systems and methods described herein have been generally described and illustrated as being implemented in association with dental procedures, other embodiments are possible. For example, the drill positioning and devices can be used to orient and position drills with respect to any of various other types of bones or surgical environments to be drill. Additionally, in some embodiments, the drill positioning devices can be used even when no implant device is to be installed.

While various advantageous aspects have been described herein as being implemented in combination with one another, other embodiments are possible. For example, each of the various aspects described herein can be implemented individually or in combination with one another. Specifically, while drill guide and surgical ring examples have been described herein having certain retention/engagement features and techniques which, in some embodiments, can help the drill guide rotate (e.g., freely rotate) within the surgical guide, it is noted that such features can be implemented without requiring such free rotation. Specifically, in some embodiments, the drill guide and/or the surgical ring can include retention features but can also limit rotation of the drill guide to a certain angular rotation. Additionally, in some embodiments, the drill guide can include handling tool retention elements alone or in combination with the retention features used to retain the drill guide within the surgical ring.

While various embodiments have been described herein, it should be understood that they have been presented and described by way of example only, and do not limit the claims presented herewith to any particular configurations or structural components. Thus, the breadth and scope of a preferred embodiment should not be limited by any of the above-described exemplary structures or embodiments, but should be defined only in accordance with the following claims and their equivalents.

What is claimed:

1. A method for forming an osteotomy site for a dental implant, the method comprising:
providing a top loading dental surgical guide comprising a template material that is configured to accommodate at least a portion of an edentulous alveolar ridge to support the orientation and guidance of surgical drills in a dental region to be drilled in a patient's mouth and a dental drill guide positioning ring housed within the template material, the dental drill guide positioning ring comprising:
a substantially cylindrical body defining a longitudinal axis and an inner surface defining a central opening; and
one or more flange retention elements extending inwardly from the inner surface of the cylindrical body, each of the one or more flange retention elements comprising:
an upper transition surface that tapers away from a to surface of the flange retention element; and
a lower engagement surface that tapers away from a bottom surface of the flange retention element that is opposite the to surface, and
providing a predetermined resisting force to temporarily retain a first drill guide within the dental drill guide positioning ring to limit axial separation of the first drill guide from the dental drill guide positioning ring;
coupling the surgical guide along the portion of the edentulous alveolar ridge such that the dental drill guide positioning ring is oriented to guide one or more surgical drills to the dental region to be drilled;
temporarily engaging the first drill guide within the dental drill guide positioning ring by axially coupling the first drill guide along its longitudinal axis with respect to the dental drill guide positioning ring, using the one or more protruding flange retention elements, independently of a rotational motion of the first drill guide relative to the dental drill guide positioning ring by engaging the one or more protruding flange retention elements within a complementary recessed feature of the first drill guide;
performing a first drilling procedure with a first drill guided by the first drill guide; and
disengaging and removing the first drill guide from the dental drill guide positioning ring.

2. The method of claim 1, wherein the axially coupling of the first drill guide comprises engaging the one or more flange retention elements within a recess of the first drill guide.

3. The method of claim 1, wherein the disengaging and removing the first drill guide comprises gripping a handling tool retention feature of the first drill guide with a handling tool.

4. The method of claim 1, wherein the first drill guide is removed from the dental drill guide positioning ring while the surgical guide remains coupled to the dental region.

5. The method of claim 1, wherein, while temporarily engaged, the first drill guide can rotate within the drill guide positioning ring without disengaging.

6. The method of claim 1, wherein the first drill guide is free of handles to be held by a user during drilling.

7. The method of claim 1, further comprising:
temporarily engaging a second drill guide within the dental drill guide positioning ring by axially coupling the second drill guide along its longitudinal axis with respect to the dental drill guide positioning ring, using the one or more protruding flange retention elements, independently of a rotational motion of the second drill guide relative to the dental drill guide positioning ring by engaging the one or more protruding flange retention elements within a recessed feature of the first drill guide; and
performing a second drilling procedure with a second drill guided by the second drill guide.

8. The method of claim 7, wherein at least one of the first drilling procedure or second drilling procedure are performed without a user handling the first drill guide or second drill guide once engaged within the dental drill guide positioning ring.

9. The method of claim 8, wherein all of the drilling procedures are performed without the user using any handled drill guides.

10. The method of claim 7, further comprising disengaging and removing the second drill guide from the dental drill guide positioning ring; and temporarily engaging a third drill guide within the dental drill guide positioning ring by axially coupling the third drill guide along its longitudinal axis with respect to the dental drill guide positioning ring, using the one or more protruding flange retention elements.

11. The method of claim 1, wherein the first drilling procedure is performed without a user handling the first drill guide once it is engaged within the dental drill guide positioning ring.

12. The method of claim 1, wherein the disengaging and removing the first drill guide from the dental drill guide positioning ring comprises gripping a feature of the first drill guide with a handling tool and pulling the first drill guide from the dental drill guide positioning ring.

13. The method of claim 12, wherein gripping the feature comprises engaging resilient elements of the handling tool onto a lip feature of the first drill guide.

14. The method of claim 13, wherein the resilient elements of the handling tool comprise finger-like elements and the lip feature of the first drill guide defines an annular recess in which the finger-like elements are disposed.

15. The method of claim 1, wherein the temporarily engaging the first drill guide within the dental drill guide positioning ring comprises gripping a feature of the first drill guide with a handling tool and inserting the first drill guide into the dental drill guide positioning ring.

16. The method of claim 15, wherein gripping the feature comprises engaging resilient elements of the handling tool onto a lip feature of the first drill guide.

17. The method of claim 16, wherein the resilient elements of the handling tool comprise finger-like elements and the lip feature of the first drill guide defines an annular recess in which the finger-like elements are disposed.

18. The method of claim 1, wherein each of the one or more flange retention elements are positioned along a common plane substantially perpendicular to the longitudinal axis of the substantially cylindrical body.

19. A method for completing a drilling procedure to form an osteotomy site for a dental implant, the method comprising:

providing a top loading dental surgical guide comprising a template material that is configured to accommodate at least a portion of an edentulous alveolar ridge to support the orientation and guidance of surgical drills in a dental region to be drilled in a patient's mouth and a dental drill guide positioning ring housed within the template material, the dental drill guide positioning ring comprising:

a substantially cylindrical body defining a longitudinal axis and an inner surface defining a central opening; and one or more flange retention elements extending inwardly from the inner surface of the cylindrical body formed along a common plane that is substantially perpendicular to the longitudinal axis, each of the one or more flange retention elements comprising:

an upper transition surface that tapers away from a to surface of the flange retention element; and a lower engagement surface that tapers away from a bottom surface of the flange retention element that is opposite the to surface, and providing a predetermined resisting force to temporarily retain a first drill guide within the dental drill guide positioning ring to limit axial separation of the first drill guide from the dental drill guide positioning ring;

coupling the surgical guide along the portion of the edentulous alveolar ridge such that the dental drill guide positioning ring is oriented to guide one or more surgical drills to the dental region to be drilled;

temporarily engaging the first drill guide within the dental drill guide positioning ring by axially coupling the first drill guide along its longitudinal axis with respect to the dental drill guide positioning ring, using the one or more protruding flange retention elements along the common plane, independently of a rotational motion of the first drill guide relative to the dental drill guide positioning ring by engaging the one or more protruding flange retention elements within a complementary recessed feature of the first drill guide, wherein the first drill guide is configured to freely rotate within the dental drill guide positioning ring;

performing a first drilling procedure with a first drill guided by the first drill guide; and disengaging and removing the first drill guide from the dental drill guide positioning ring.

* * * * *

UNITED STATES PATENT AND TRADEMARK OFFICE
CERTIFICATE OF CORRECTION

PATENT NO.         : 9,211,165 B2                                          Page 1 of 1
APPLICATION NO.    : 14/679285
DATED              : December 15, 2015
INVENTOR(S)        : Jamison It is certified that error appears in the above-identified patent and that said Letters Patent is hereby corrected as shown below:

In the claims

Claim 1 line 5 column 18, delete "from a to"

and insert --from a top--.

Claim 1 line 9 column 18, delete "the to surface"

and insert --the top surface--.

Claim 19 line 14 column 20, delete "from a to"

and insert --from a top--.

Claim 19 line 18 column 20, delete "the to surface"

and insert --the top surface--.

Signed and Sealed this
Fourteenth Day of June, 2016

Michelle K. Lee
*Director of the United States Patent and Trademark Office*